(12) United States Patent
Scaboo et al.

(10) Patent No.: US 10,401,317 B2
(45) Date of Patent: Sep. 3, 2019

(54) WIRELESSLY SENSING PROPERTIES OF A CLOSED ENVIRONMENT AND DEVICES THEREOF

(71) Applicant: Gate Scientific, Inc., Milpitas, CA (US)

(72) Inventors: Kristian Michael Scaboo, Castro Valley, CA (US); Morten Juel Jensen, Saratoga, CA (US)

(73) Assignee: Gate Scientific, Inc., Milpitas, CA (US)

( * ) Notice: Subject to any disclaimer, the term of this patent is extended or adjusted under 35 U.S.C. 154(b) by 0 days.

(21) Appl. No.: 15/882,909

(22) Filed: Jan. 29, 2018

(65) Prior Publication Data

US 2018/0195989 A1 Jul. 12, 2018

Related U.S. Application Data

(63) Continuation-in-part of application No. PCT/US2017/042435, filed on Jul. 17, 2017.
(Continued)

(51) Int. Cl.

| | |
|---|---|
| *G01N 9/36* | (2006.01) |
| *B01F 13/08* | (2006.01) |
| *H05B 6/06* | (2006.01) |
| *G01N 27/12* | (2006.01) |
| *C12M 1/06* | (2006.01) |
| *G01N 25/48* | (2006.01) |

(Continued)

(52) U.S. Cl.
CPC .......... *G01N 27/123* (2013.01); *B01F 7/162* (2013.01); *B01F 13/08* (2013.01); *B01F 13/0818* (2013.01); *B01F 15/00175* (2013.01); *B01F 15/00266* (2013.01); *B01F 15/00285* (2013.01); *B01F 15/00396* (2013.01); *C12M 27/02* (2013.01); *G01N 9/36* (2013.01); *G01N 25/482* (2013.01); *G01N 27/4167* (2013.01); *H05B 6/06* (2013.01)

(58) Field of Classification Search
CPC .............................. G05B 15/02; A47J 36/165
USPC ....................... 700/11; 99/325, 342; 219/201
See application file for complete search history.

(56) References Cited

U.S. PATENT DOCUMENTS

| | | |
|---|---|---|
| 3,748,845 A | 7/1973 | Mutter et al. |
| 4,042,219 A | 8/1977 | Terry |

(Continued)

FOREIGN PATENT DOCUMENTS

| | | |
|---|---|---|
| DE | 3322409 | 1/1985 |
| DE | 4201693 | 4/1993 |

(Continued)

OTHER PUBLICATIONS

10 Instruments Win Pittcon's 2018 Excellence Awards, https://www.laboratoryequipment.com/article/2018/03/10-instruments-win-pittcons-2018-excellence-awards, 5 pages, accessed on Jun. 1, 2018.

(Continued)

*Primary Examiner* — Michael J Brown
(74) *Attorney, Agent, or Firm* — Levine Bagade Han LLP

(57) ABSTRACT

A wireless sensor measures properties of a substance and transmits the properties to a remote wireless receiver. The wireless sensor can be fully enclosed within a container containing the substance, allowing remote monitoring of the properties of the substance without compromising integrity of a closed system.

30 Claims, 16 Drawing Sheets

Related U.S. Application Data

(60) Provisional application No. 62/362,737, filed on Jul. 15, 2016.

(51) Int. Cl.
  G01N 27/416 (2006.01)
  B01F 7/16 (2006.01)
  B01F 15/00 (2006.01)
  G05B 15/02 (2006.01)

(56) References Cited

U.S. PATENT DOCUMENTS

| | | | |
|---|---|---|---|
| 5,120,135 | A | 6/1992 | Ullman |
| 5,691,687 | A | 11/1997 | Kumagai et al. |
| 5,814,900 | A | 9/1998 | Esser et al. |
| 6,065,865 | A | 5/2000 | Eyraud et al. |
| 6,149,295 | A | 11/2000 | Volkmer et al. |
| 6,432,706 | B1 | 8/2002 | Hudson et al. |
| 6,698,923 | B2 | 3/2004 | Bedetti et al. |
| 7,140,239 | B2 | 11/2006 | Greenwood et al. |
| 8,122,815 | B2 | 2/2012 | Wolfe |
| 2004/0050836 | A1* | 3/2004 | Nesbitt ............... G01N 35/04 219/201 |
| 2004/0159244 | A1* | 8/2004 | Leason ............... A47J 36/165 99/348 |
| 2005/0182342 | A1 | 8/2005 | Dinsmoor et al. |
| 2012/0223573 | A1* | 9/2012 | Schatz ............... H02J 5/005 307/9.1 |
| 2014/0056325 | A1* | 2/2014 | Guerra ............... G01K 7/24 374/1 |
| 2014/0217091 | A1* | 8/2014 | Ho ............... H02J 50/10 219/660 |
| 2014/0263287 | A1 | 9/2014 | Widitora et al. |

FOREIGN PATENT DOCUMENTS

| | | |
|---|---|---|
| DE | 4423848 | 1/1996 |
| DE | 4440250 | 5/1996 |
| EP | 0988888 | 3/2000 |
| JP | 63012936 | 1/1988 |
| JP | 63151342 | 6/1988 |
| JP | 02139024 | 5/1990 |
| JP | 2000124030 | 4/2000 |
| WO | WO 1998/052350 | 11/1998 |
| WO | WO 2018/014031 | 1/2018 |
| WO | WO 2018/014032 | 1/2018 |

OTHER PUBLICATIONS

Motivation Through Recognition: Awards and Other Highlights From Pittcon 2018, https://www.americanlaboratory.com/Blog/349653-Motivation-Through-Recognition-Awards-and-Other-Highlights-From-Pittcon-2018/, 3 pages, accessed on Jun. 1, 2018.
Pittcon Conference & Expo First Annual Pittcon Today Excellence Awards—Pittcon, https://pittcon.org/excellence-award-winners/, 3 pages, accessed on Jun. 1, 2018.
PittconWeds18, http://viewer.zmags.com/publication/7726c869#/7726c869/4, 1 page, accessed on Jun. 1, 2018.

* cited by examiner

WIRELESSLY SENSING PROPERTIES OF A CLOSED ENVIRONMENT AND DEVICES THEREOF

CROSS-REFERENCE TO RELATED APPLICATION

This application is a continuation-in-part of International Application No. PCT/US2017/042435, filed Jul. 17, 2017, which claims priority to U.S. Provisional Application No. 62/362,737, filed Jul. 15, 2016, both of which are incorporated by reference herein in their entireties.

BACKGROUND (1) Field of the Invention

This disclosure relates to measuring and regulating properties of contents of a closed environment.

(2) Description of the Related Art

Numerous processes rely upon observation of contents of a closed environment in order to monitor and control the processes. For example, in a laboratory setting, a substance may be heated in a closed container to facilitate a desired chemical reaction or physical change. These closed containers may be heated using a hotplate stirrer, which can mix substances or keep them homogeneous while holding them at a certain temperature. Maintaining the temperature in these substances as they are mixed can be complicated by factors such as inconsistent transfer of heat from the hotplate to the substance as well as fluctuations in room temperature or hotplate power. Users of a hotplate may therefore use an external temperature probe to monitor the temperature of the substance. Some hotplates have temperature probes built into the plate that can measure the temperature of the heating plate surface. However, due to inconsistent thermal contact between the plate and the container, as well as inconsistent heat transfer to the substance inside the container, the built-in temperature probes typically have low accuracy. Other methods for measuring temperature include lowering a temperature probe into the sample, using a support structure external to the container, to directly measure the temperature of the substance. However, ensuring the probe remains in contact with the substance can be difficult, especially as the substance is mixed or agitated. Furthermore, if the container holding the substance needs to be closed during the heating and mixing process, lowering an external probe into the container can compromise the integrity of the process.

Other closed systems can similarly complicate measurement of properties of the system. There is therefore a need for a method to detect properties of a closed system, without compromising the integrity of the system.

SUMMARY

A wireless sensor measures properties of a substance and transmits the properties to a remote wireless receiver. The wireless sensor can be fully enclosed within a container containing the substance, allowing remote monitoring of the properties of the substance without compromising integrity of a closed system.

The wireless sensor can be incorporated into a stir bar device, which can be magnetically manipulated by an instrument to agitate a fluid in a container. The instrument can also heat the fluid in the container. As the stir bar device agitates the fluid, the device can measure properties of the fluid and transmit the properties to a control system of the instrument. The control system can regulate outputs of the instrument, such as an amount of heat or a rate of rotation of the stir bar device, based on feedback received from the wireless sensor in the stir bar device. Because the stir bar device wirelessly transmits data to the control system, the container can be sealed.

A wireless sensor can be used in systems to remotely monitor and control properties of substances.

An instrument is disclosed that can have an agitator, a temperature sensor and a controller. The agitator can be configured to agitate a liquid in a container. The temperature sensor can be immersible in the liquid. The temperature sensor can be configured to measure a temperature of the liquid. The temperature sensor can wirelessly transmit feedback indicating the temperature of the liquid to a wireless receiver. The controller can be configured to regulate the temperature of the liquid based on the feedback.

An instrument is disclosed that can have a wireless sensor and a wireless receiver. The wireless sensor can be enclosed within a closed container containing a substance. The wireless sensor can have a wireless transmitter. The wireless sensor can have a sensor configured to measure a property of the substance. The wireless receiver can be in electronic communication with the wireless transmitter. The wireless transmitter can transmit data describing the property of the substance to the wireless receiver.

A wireless temperature measurement device is disclosed. The wireless temperature measurement device can be configured to work as an agitator that can be dropped into liquid. The liquid can be heated or cooled by an instrument. The instrument can communicate with and power the measurement device wirelessly. The device can measure the temperature of the liquid.

The wireless temperature measurement device can have a wireless temperature sensor device configured to communicate with a receiver via wireless communication. The sensor device can have at least one of the following properties: a) the sensor device is powered with wireless energy; b) the sensor device agitates liquid by use of magnetic action; c) the sensor device has at least 2 different temperature measurement elements that can be compared and if they do not track then the device is considered broken or out of calibration; d) at least one of the temperature measurement elements is configured to operate by measuring the resistance change in a thermistor; and/or e) at least one of the temperature measurement elements is configured to operate by measuring the change in voltage of a semiconductor device.

The device can be completely immersed into the liquid. The measurement device may not require any wires to function. The wireless temperature measurement device can have at least one of the following properties: a) the measurement device communicates with the instrument via wireless signals and the measurement device is powered with wireless energy; b) the liquid to be heated is contained in a separate container that can be placed on or at the instrument; c) the measurement device also functions as an agitator of the liquid to be heated and the instrument activates the agitator function via a magnetic field; and/or d) the measurement device also measures at least one other liquid characteristic, said at least one other characteristic being any of pH, Specific gravity, viscosity, salinity, conductance, color, absorbance, fluorescence, pressure, electrochemical, conductivity, chemiluminescence, liquid level, rotation, acceleration or velocity.

The measurement device can be completely immersed into the liquid. The measurement device can measure the temperature of the liquid. The wireless measurement device can have at least one of the following properties: a) the measurement device communicates with the instrument via radio waves and the measurement device is powered with radio waves; b) the liquid to be agitated is contained in a separate container that can be placed on or at the instrument; c) the measurement device also functions as an agitator of the liquid to be heated and where the instrument can activate the agitator function via a magnetic field; d) the measurement device also measures other liquid characteristics such as any of pH or fluid velocity; e) the measurement device also measures at least one other characteristic of the fluid, said at least one other characteristic being any of pH, Specific gravity, viscosity, salinity, conductance, color, absorbance, fluorescence, pressure, electrochemical, conductivity, chemiluminescence, liquid level, rotation or velocity.

A system is disclosed where a fluid disposed inside of a sealed container is automatically measured remotely for at least one measurement without direct electrical connection. The system can have at least one of: a) the at least one measurement is done using wireless communication and wireless powering of the sensor, at least one measurement being any of temperature, electrochemical, pH, specific gravity, viscosity, conductance, salinity, color, absorbance, fluorescence, pressure, conductivity, chemiluminescence, liquid level, rotation, velocity and acceleration; and/or b) the at least one measurement is done using wireless or optical communication to a wirelessly or optically powered sensor, said at least one measurement being any of temperature, electrochemical, pH, specific gravity, viscosity, conductance, salinity, color, absorbance, fluorescence, pressure, conductivity, chemiluminescence, liquid level, rotation, velocity and acceleration.

A system for manipulating a liquid compound based on the feedback from a wireless sensor element that can measure one or more parameters in the liquid is disclosed. The liquid manipulation can be by heating, agitation, mechanical homogenization, electrolysis, adding another compound exposing to electromagnetic waves comprising any of light or radio waves or x-rays, exposing to radiation, exposing to pressure or vacuum exposing to sound waves or ultrasound waves, exposing to centrifugal force, exposing to an electric field, exposing to a magnetic field, removing selective constituents by filtering or density separation of certain compounds, removing bulk liquid, degassing, desalination; and wherein said feedback is obtained from at least one wireless measurement, said at least one wireless measurement being any of temperature, electrochemical, pH, specific gravity, viscosity, conductance, salinity, color, absorbance, fluorescence, pressure, conductivity, chemiluminescence, liquid level, rotation, velocity, acceleration, or combinations thereof.

A system is disclosed that can have a container that can have an embedded wireless temperature sensor and a separate communication device that can communicate with the wireless temperature sensor. The system can have any of: a) the embedded wireless temperature sensor is also powered with wireless power; b) the communication device is configured to heat the container; c) the communication device can be set to heat the container based on the temperature feedback transmitted wirelessly; d) the container has built in mechanical blades for homogenization or heating the material in the container and where the communication device has an activation element configured to activate the mechanical blades; e) the communication device can be set to activate the blades in the container based on the temperature feedback transmitted wirelessly.

A system is disclosed where a substance disposed inside of a sealed container can be automatically measured remotely with a wireless sensor for at least one measurement without direct electrical connection. The system can have at least one of: a) the at least one measurement is done using wireless communication and wireless powering of the sensor, at least one measurement being any of temperature, electrochemical, pH, specific gravity, viscosity, conductance, salinity, color, absorbance, fluorescence, pressure, conductivity, chemiluminescence, fill level, rotation, velocity and acceleration; b) the at least one measurement is done using wireless or optical communication to a wirelessly or optically powered sensor, said at least one measurement being any of temperature, electrochemical, pH, specific gravity, viscosity, conductance, salinity, color, absorbance, fluorescence, pressure, conductivity, chemiluminescence, fill level, rotation, velocity and acceleration; c) the at least one measurement is done using wireless or optical communication to a sensor, said at least one measurement being temperature and specific gravity of the fluid; or combinations thereof. The disclosed system can also have: a wireless sensor that contains a wireless transmitter for transmitting sensor data to a wireless receiver and where the wireless receiver is a computing device such as a smart phone; and where the wireless sensor can measure temperature and specific gravity of the substance in the container. The system can have any of the following: A) the wireless receiver computing device that receives the wireless sensor data can emit a notification if the temperature of the substance is outside specified limits; B) the wireless receiver computing device that receives the wireless sensor data can emit a notification if the specific gravity of the substance is outside specified limits; C) the wireless receiver computing device has pre-select profiles that sets parameters for durations and specified temperature limits for the substance and where the wireless receiver computing device emits a notification if the substance parameters are outside the profile parameters; D) the wireless receiver computing device has pre-select profiles that sets parameters for durations and specified temperature limits and specified specific gravity limits for the substance and where the wireless receiver computing device emits a notification if the substance parameters are outside the profile parameters; E) the wireless sensor data is presented to the wireless receiver computing device in the form of a web page using standard web language such as HTML; F) the wireless receiver computing device processes an application program that interpret and presents the wireless sensor data; G) the wireless sensor transmits sensor data through one or more wireless routers to the wireless receiver computing device; H) the wireless sensor is made to float on or at the top of the substance in the container; or combinations thereof.

An instrument device is disclosed for heating and agitating a liquid in a separate container and a wireless measurement device that can be dropped into the liquid to be heated and where the instrument communicates with and powers the measurement device wirelessly and can thereby measure at least one property of the liquid, wherein the liquid is agitated by magnetic action by a separate encapsulated magnet that is dropped into the liquid, and wherein the measurement device can float near or at the top of the liquid, and wherein the measurement device measures at least one property of the liquid, said at least one property of the liquid being any of pH, Specific gravity, viscosity, salinity, conductance, color, absorbance, fluorescence, pressure, electrochemical, conductivity, chemiluminescence, liquid level, rotation or velocity.

DETAILED DESCRIPTION

Figure 1:
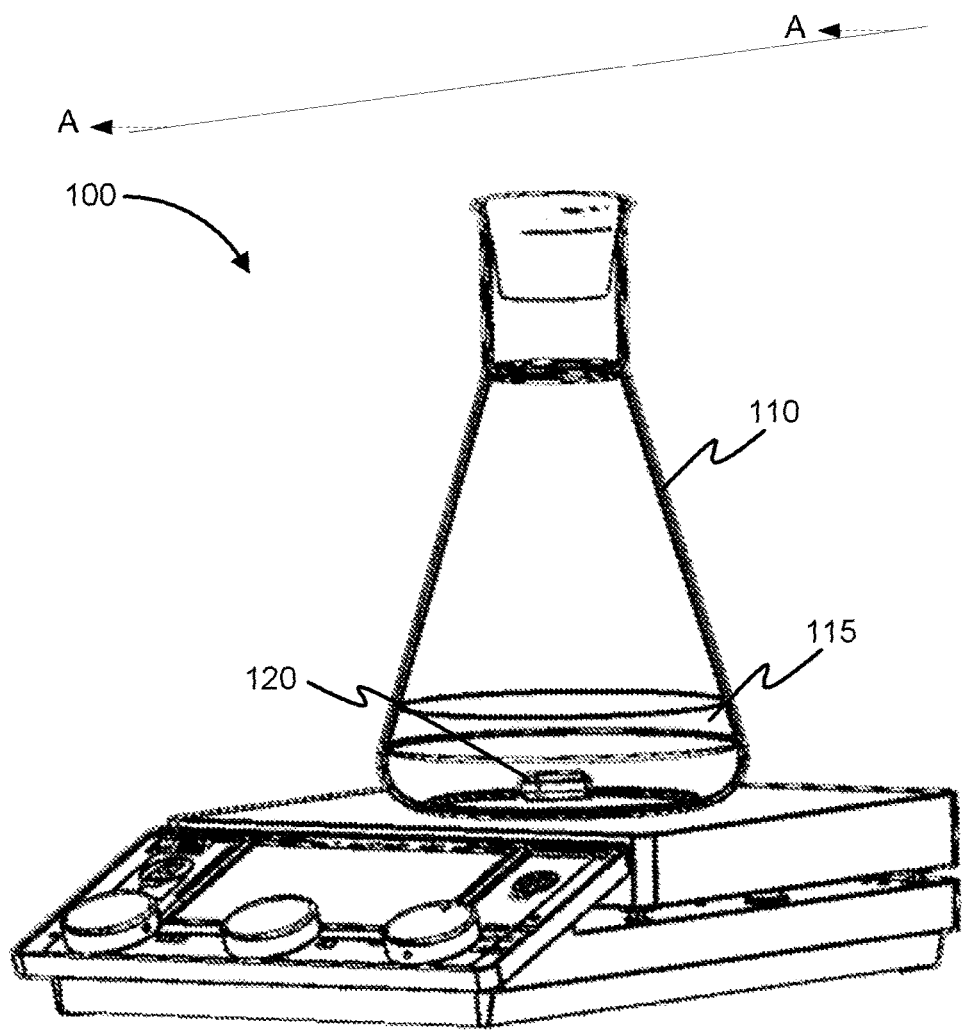
FIG. 1 is a perspective view a system for measuring and regulating properties of contents of a closed container.

FIG. 1 illustrates that a system 100 for measuring and regulating properties of contents of a closed container can have a container 110 containing a substance 115 and a sensing device 120. The container 110 can be a closed or partially closed environment. For example, the container 110 can be a flask, vial, or pot that can contain the substance 115 and can be closed via a stopper or lid to form an airtight environment. The container 110 may be closable with a stopper or lid to form an environment that is not airtight, or may be open to the ambient environment. Other examples of the container 110 include a blender pitcher, a fermenting vessel, a bottle, a well plate, or any other container suitable to contain the substance 115.

The substance 115 can include any liquid, solid, gel, gas, or combination of materials. Properties of the substance 115 can be changed and controlled by the system 100 based on data detected by the sensing device 120. Data describing properties of the substance 115 can be wirelessly transmitted by the sensing device 120 to a wireless receiver outside the container 110.

The sensing device 120 can be fully enclosed in the container 110, and some configurations of the sensing device 120 can be fully or partially immersible in the substance 115. The sensing device 120 can be supported by and fully contained within the container 110, or may cross through the container 110 without compromising the integrity of a closed environment in the container 110. The sensing device 120 may be wirelessly powered by an external wireless receiver, enabling the sensing device 120 to function without a battery. Because a battery requires periodic charging, can wear out after a number of charges, and typically operates most effectively within a limited temperature range, omitting a battery from the sensing device 120 improves the longevity of the device and can be used for applications that may exposes the device 120 to extreme temperatures. The sensing device 120 can include a battery.

Figure 2:
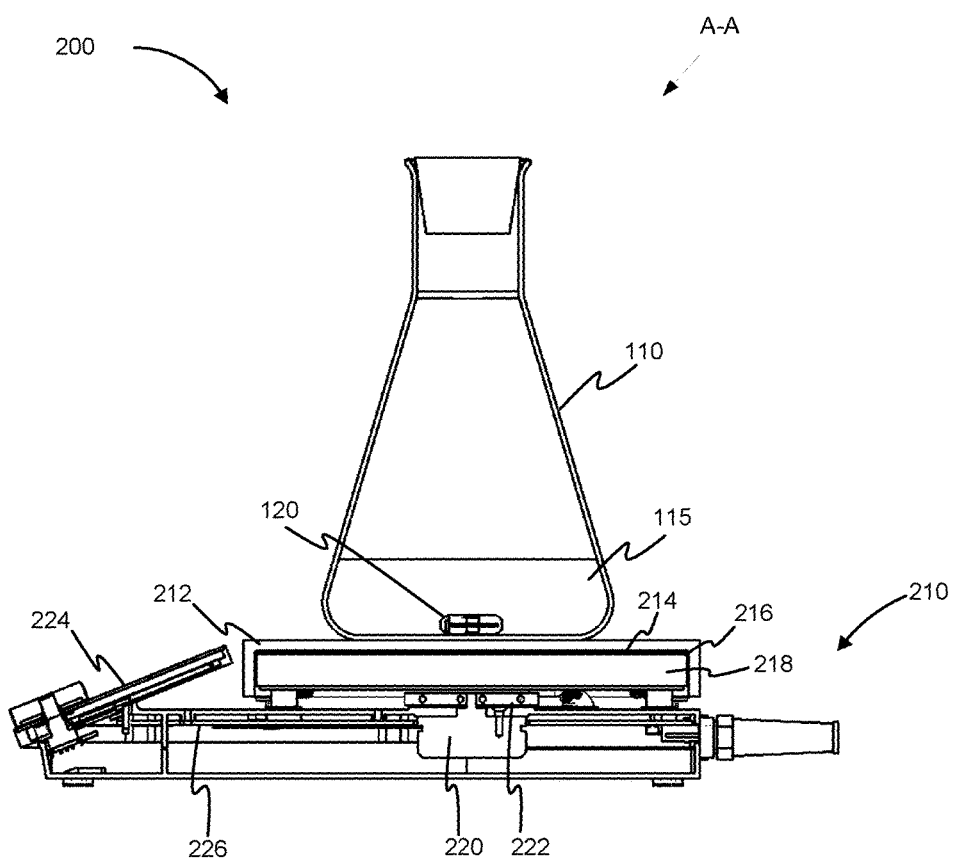
FIG. 2 is a variation of cross-section A-A of FIG. 1.

FIG. 2 shows an example configuration 200 of the system 100, along cross-section A-A shown in FIG. 1. The system 200 can be a system for heating and agitating a substance 115 in a container 110, and can include an instrument 210 and the sensing device 120.

The instrument 210 can include a heating surface 212 for supporting the container 110 and transferring heat from a heating element 216 to the container 110 and substance 115. A wireless receiver 214 can be positioned under the heating surface 212 and electrically and thermally insulated from the heating element 216 or the heating element 216 can be combined with the wireless receiver 214. Under the heating element 216 can be an insulating layer 218. The instrument 210 can also include a magnet 222 rotatable by a motor 220.

The magnet 222 can cause a magnetic object placed on or near the heated surface 212 to rotate as the magnet 222 is rotated by the motor 220. Accordingly, a magnetic object placed in the container 110 can agitate or mix the substance 115 as it is rotated by the magnet 222. The sensing device 120 can include a corresponding magnet, enabling the sensing device 120 to function as an agitator of the substance 115, or a magnet separate from or coupled to the sensing device 120 may be placed into the container 110. The magnetic action can also be accomplished by electromagnets placed under or near the heating surface 212.

The instrument 210 can also include a control panel 224 configured to receive user inputs and display information to the user. For example, the control panel 224 can receive user inputs to increase or decrease a temperature of the heating element 216 and increase or decrease a rate of rotation of the magnet 222. The control panel 224 can include a display, such as an LCD screen or electronic ink (E Ink) screen or one or more LEDs, that can display temperature, magnet rotation, or other information to the user. The control panel 224 can additionally or alternatively include buttons, knobs, or other input devices enabling a user to provide input into the instrument 210.

A controller 226 in the instrument 210 can control the instrument 210, processing inputs received from a user and feedback received from the wireless receiver 214. Outputs of the instrument 210, such as the thermal energy emitted by the heating element 216 and a rate of rotation of the motor 220, can be controlled by the controller 226 based on feedback received from the sensing device 120 and/or other sensing devices in the instrument 210.

The wireless receiver 214 can be configured to receive data transmitted wirelessly from the sensing device 120. The wireless receiver 214 can be, for example, a radio frequency identification (RFID) receiver, a near field communication (NFC) receiver, a Bluetooth receiver, a Bluetooth Low Energy receiver, a ZigBee receiver, a Z-Wave receiver or a Wi-Fi receiver or a receiver of any other wireless protocol. Data received by the wireless receiver 214 can be stored in a memory or received by a processor for controlling outputs of the instrument 210 based on the received data. The wireless receiver 214 can also wirelessly power the sensing device 120 via radio signals or inductive charging. Properties of the substance 115, such as temperature, pH, specific gravity, viscosity, salinity, conductance, absorbance, fluorescence, or pressure, can be measured by the sensing device 120 and transmitted to the wireless receiver 214.

Figure 3A:
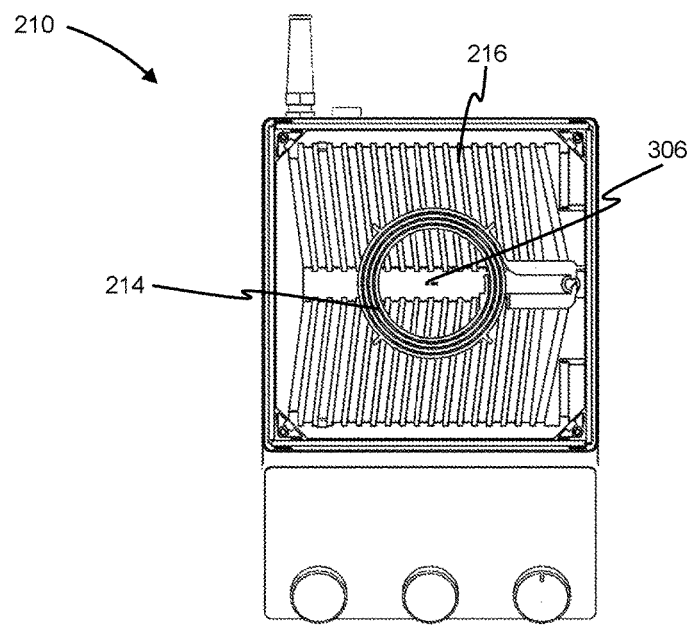
FIG. 3A is a partial see-through top view of a variation of an instrument in the system.

FIG. 3A illustrates an example top view of the instrument 210 with the heating surface 212 removed. As shown in FIG. 3A, the wireless receiver 214 can be placed between the heating element 216 and the heating surface 212. One or more temperature sensors 306 can measure the temperature of the heating element 216 or the heating surface 212. The temperature sensors 306 can use multiple different sensor types to verify calibration or ensure accuracy of the temperature measurements of the heating surface 212. For example, one temperature sensor 306 can be a platinum resistance temperature detector (RTD), and the other temperature sensor 306 can be a thermocouple.

Figure 3B:
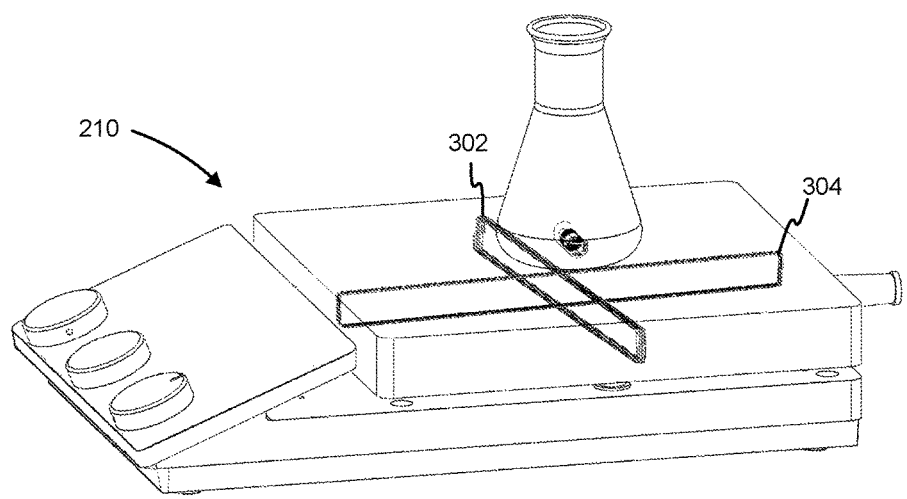
FIG. 3B is a partial see-through perspective view of a variation of an instrument in the system.

FIG. 3B illustrates that the wireless receiver 214 can include a first antenna 302 and a second antenna 304 configured to receive data from, and optionally to transmit data to, the sensing device 120. The first and second antennas 302 and 304 can have different orientations to detect signals from the sensing device 120 in any rotational position of the sensing device 120. Additional or fewer antennas may be included in the instrument 210. The antenna can be made from high temperature Ceramawire or other materials that can withstand the temperature near at the antenna.

Figure 4:
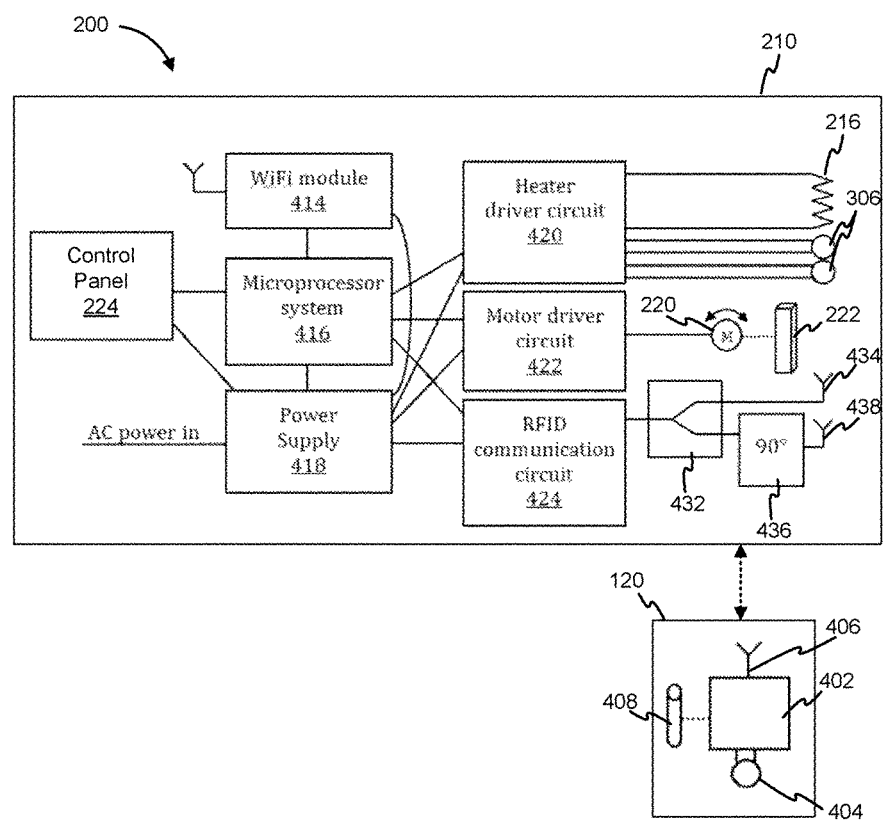
FIG. 4 is a schematic diagram illustrating an example electronic configuration of a system for measuring and regulating properties of contents of a closed container.

FIG. 4 is a schematic diagram illustrating that the sensing device 120 can include an integrated circuit 402 that can read output from a sensor 404 and communicate with an antenna 406. The integrated circuit 402 can contain an internal temperature sensor such as a semiconductor junction. The integrated circuit 402 can include an Analog to Digital converter to convert the signals from the sensors to data for wireless transmission. A magnet 408 can be mechanically coupled to the integrated circuit 402, for example by a housing enclosing the magnet 408 and the integrated circuit 402.

The instrument 210 can include a control panel 224, a WiFi module 414, a microprocessor system 416, a power supply 418, a heater driver circuit 420, a motor driver circuit 422, and a communication circuit 424. Other variations can include additional, fewer, or different components. The microprocessor system 416, WiFi module 414, heater driver circuit 420, motor driver circuit 422, and RFID communication circuit 424 can collectively form the controller 226 described with respect to FIG. 2.

The power supply 418 receives power from an input, such as an AC power source, and provides power to other components of the instrument 210.

Functions of the instrument 210 can be controlled by the microprocessor system 416. The microprocessor system 416 can be, for example, an ARM-based microprocessor system with random access memory, flash memory as well as clock source and other circuits needed to create a microprocessor system, and can include a microprocessor as well as a volatile or non-volatile memory. The microprocessor system 416 can communicate with the control panel 224 to display information or receive user inputs, and can control the heater driver circuit 420 and the motor driver circuit 422. The microprocessor system 416 can also communicate with the RFID communication circuit 424 and the WiFi module 414 to receive data transmitted to the WiFi module 414 or the RFID communication circuit 424, or to transmit data from the WiFi module 414 or the RFID communication circuit 424.

The heater driver circuit 420 drives the heating element 216 to provide heat to the heating surface 212. The heater driver circuit 420 can regulate the temperature of the heating element 216 based on inputs received from the one or more temperature sensors 306. The heater driver circuit 420 can also regulate the temperature of the heating element 216 based on data received from the microprocessor system 416, such as a temperature of the substance 115 detected by the sensing device 120.

The motor driver circuit 422 drives the motor 220, which in turn rotates the magnet 222 at various speeds and in both directions. A rate of rotation of the magnet 222 can be communicated to the motor driver circuit 222 by the microprocessor system 416, based on a user input received at the control panel 224.

The RFID communication circuit 424 can receive a signal from and transmit a signal to a remote wireless device, such as the sensing device 120. The RFID communication circuit 424 can provide an electronic signal to the sensing device 120 to power the sensing device 120. A signal output by the RFID communication circuit 424 can pass through a splitter 432, which passes the split signal to a first antenna 434 and a 90-degree phase shifter 436 and second antenna 438. The 90-degree phase shift can enable the RFID communication circuit 424 to communicate with the sensing device 120 when the sensing device 120 is in any rotational position. Alternatively, if there is only one antenna in the system, the output from the RFID communication circuit 424 can go directly to the one antenna eliminating the need for a splitter 432 and a 90-degree phase shift 436 and second antenna 438.

Sensing Device

Figure 5A:
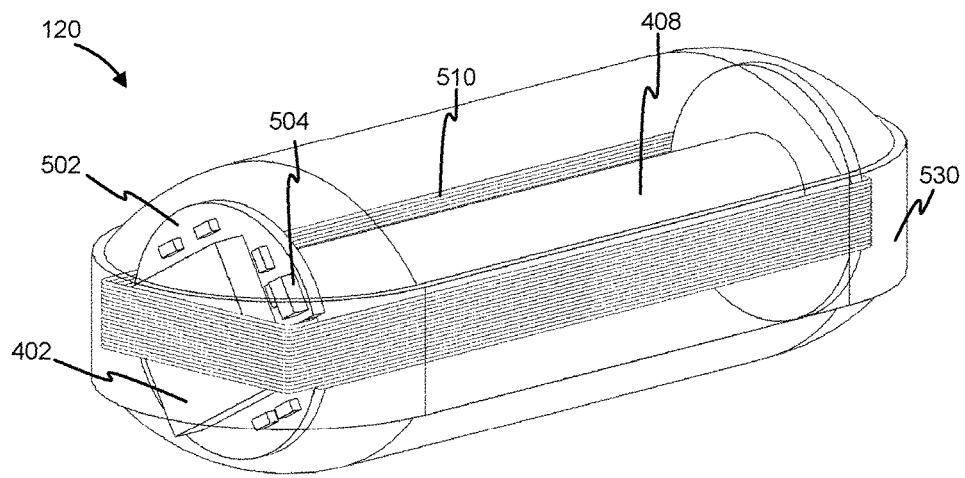
FIGS. 5A-5B illustrate example configurations of sensing devices configured to measure temperature.
Figure 5B:
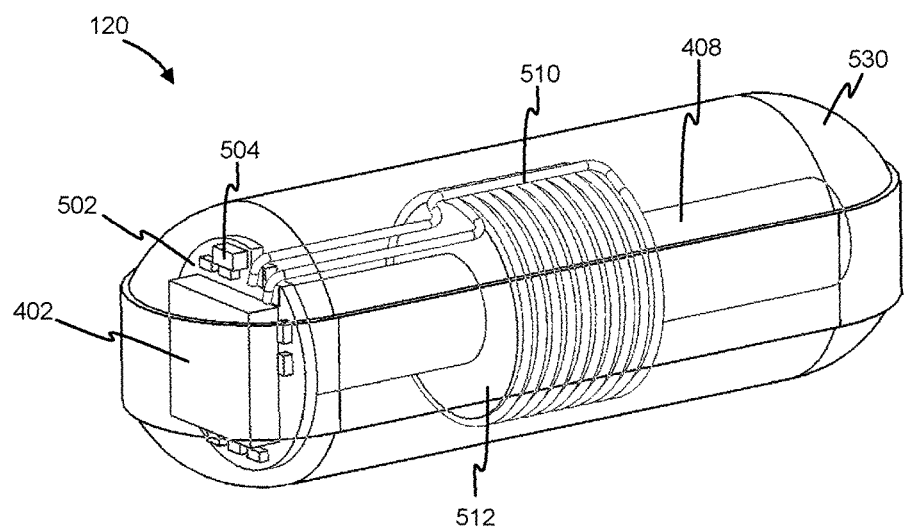

FIGS. 5A-5B illustrate examples of the sensing device 120 configured to measure the temperature of the substance 115. The sensing device 120 can include a circuit board 502 supporting the integrated circuit 402 and a thermistor 504 readable by the integrated circuit 402. A resistance of the thermistor 504 can change in response to a temperature in the substance 115, and the integrated circuit 402 can determine the temperature of the substance 115 by measuring the resistance. The integrated circuit 402 may also have an internal temperature sensor like a semiconductor junction, to which the temperature measured by the thermistor 504 can be compared. By having temperature being measured by two different temperature sensor types, aging, calibration, and other reliability issues can be determined because the effect of these reliability issues will likely be different on the two different temperature sensor types. An internal coil 510, comprising for example 40 AWG copper wire, can form an antenna for the sensing device 120. As shown in FIG. 5A, the internal coil 510 can be wound longitudinally within the sensing device 120. FIG. 5B illustrates that the internal coil 510 can be wound around a ferrite tube 512 concentric to a longitudinal axis of the sensing device 120.

The sensing device 120 can further include the magnet 408, enabling the sensing device 120 to agitate or mix the substance 115 in the container 110. A casing 530 can encapsulate the circuit board 502, internal coil 510, and magnet 408. Many types of encapsulations may be used for the casing 530, such as plastics, glass, rubber, or other materials that can provide a barrier between the substance 115 and electronics internal to the sensing device 120. For example, the casing 530 can be constructed from EFEP from Daikon™, which is a fluoropolymer with a relatively low processing temperature point around 230° C.

The sensing device 120 shown in FIG. 5B can be used to measure viscosity of the substance 115, in addition to measuring the temperature. A wireless receiver, such as the antenna 302 and antenna 304 of the instrument 210, can be oriented perpendicularly to the internal coil 510. As the sensing device 120 is rotated via the magnet 408, the wireless receiver can detect an orientation of the internal coil 510. A rate of the sensing device's rotation can be calculated based on the orientations, and a torque on the motor 220 can be measured. Based on the rate of rotation and the torque on the motor 220, viscosity of the substance 115 can be determined. The rate of rotation of the sensing device 120 can be measured in other manners, such as with a gyroscope or accelerometer.

Figure 6A:
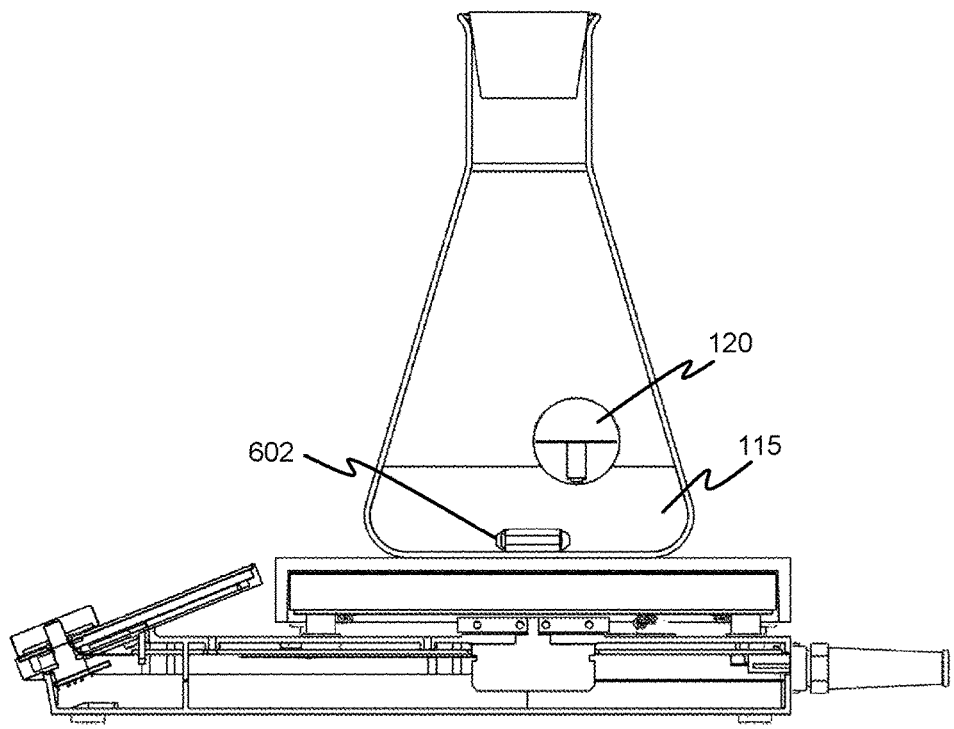
FIGS. 6A-6B illustrate an example floatable sensing device.
Figure 6B:
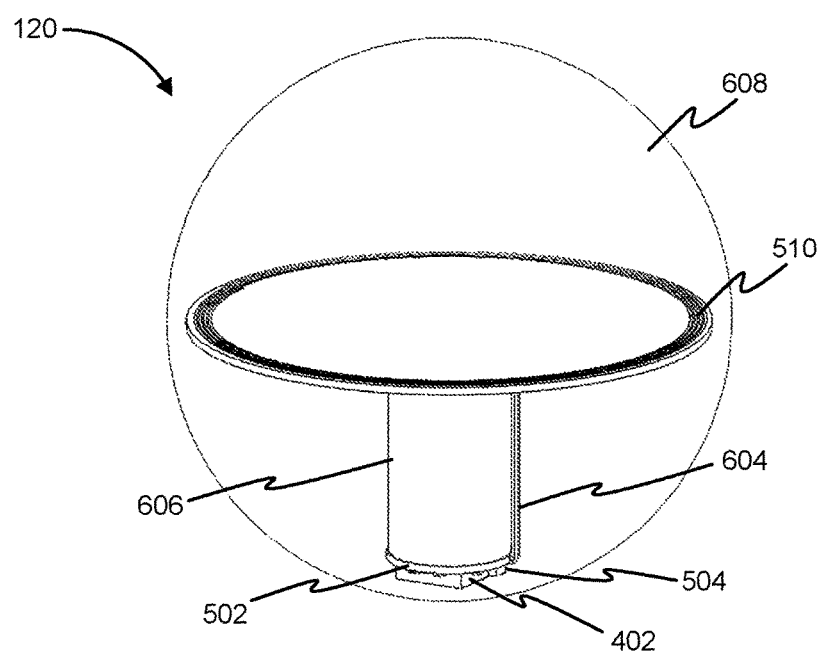

FIG. 6A illustrates another example of the sensing device 120 that is configured to float on the substance 115. An agitator 602 separate from the sensing device 120, such as a magnetic stir bar, can be used to agitate the substance 115 as described above. FIG. 6B illustrates components of the floatable sensing device 120 configured to sense temperature of the substance 115. As shown in FIG. 6B, the floatable sensing device 120 can include the antenna coil 510, the circuit board 502, the thermistor 504, and the integrated circuit 402. Antenna wires 604 can couple the antenna coil 510 to the integrated circuit 402. A ballast 606 stabilizes the sensing device 120, and a plastic overmold 608 encapsulates the electronics and ballast 606. The floatable sensing device 120 can measure the temperature of the substance 115 and transmit the detected temperature to a wireless receiver via the antenna coil 510. Although the floatable sensing device 120 shown in FIG. 6B is a temperature sensor, sensors measuring other properties of the substance 115 can be provided in the floatable sensing device 120 instead of, or in addition to, the temperature sensing components.

Figure 7:
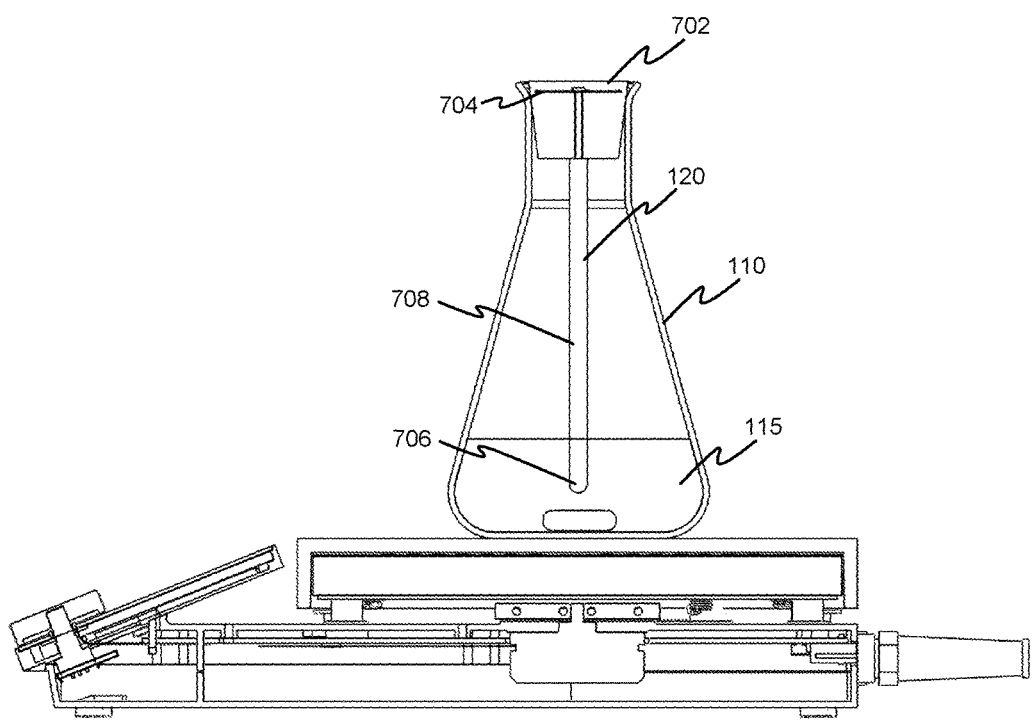
FIG. 7 illustrates an example sensing device coupled to a stopper of the closed container.

FIG. 7 illustrates an example sensing device 120 that is coupled to a stopper 702 closing or sealing a top opening of the container 110. A wireless circuit and antenna 704 can be housed in the stopper 702, and can be coupled to a sensor 706 in contact with the substance 115 by a shaft 708. The sensor 706 can measure properties of the substance 115 and communicate the properties to the wireless circuit and antenna 704, which in turn can transmit data describing the properties to an external receiver. Similar configurations of the sensing device 120 may be provided in a lid or other enclosure, or the container 110 itself, rather than in a stopper 702.

Figure 8:
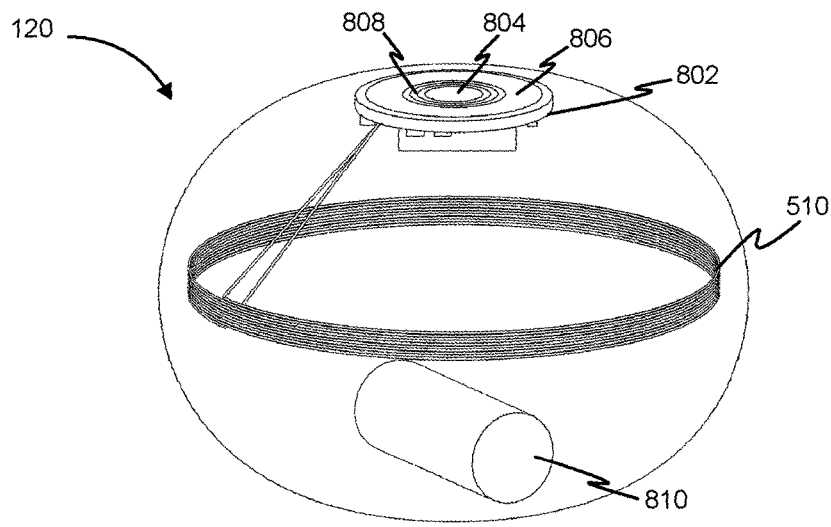
FIG. 8 illustrates an example sensing device configured as a wireless electrochemical sensor.

FIG. 8 illustrates an example sensing device 120 configured as a wireless electrochemical sensor. As shown in FIG. 8, the electrochemical sensor can include a wireless communication circuit 802, a measuring electrode 804, a counter electrode 806, and a reference electrode 808. The wireless communication circuit 802 can receive a voltage difference between the measuring electrode 804 and the counter electrode 806, and report the voltage difference to a wireless receiver via the antenna 510. Based on the voltage data, the wireless communication circuit 802 or a remote system can determine an electrochemical property of the substance 115, which can indicate properties such as a concentration of glucose or alcohol in the substance. The wireless communication circuit 802 can also maintain a stable voltage at the measuring electrode 804 using the reference electrode 808 and a potentiostat embedded in the wireless communication circuit 802 (not shown in FIG. 8). The sensing device 120 can further include a magnet and/or ballast 810 allowing the sensing device 120 to function as an agitator and/or stabilizing the sensing device 120. The device in FIG. 8 can also be used for conductivity measurement of substance 115 by measuring the conductivity between two electrodes when a specific voltage is applied across them.

Figure 9:
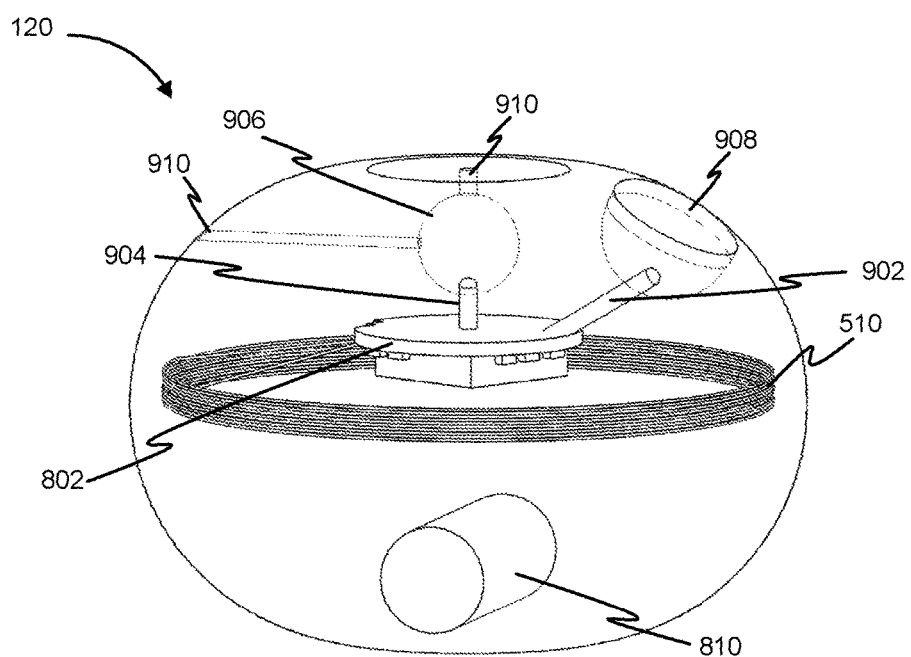
FIG. 9 illustrates an example sensing device configured as a wireless pH sensor.

FIG. 9 illustrates an example sensing device 120 configured as a wireless pH sensor. As shown in FIG. 9, the pH sensor can include the wireless communication circuit 802, a first electrode 902, a second electrode 904, a reference electrolyte 906, H+ selective glass 908, and a porous junction 910. The H+ selective glass 908 is sensitive to hydrogen ions in the substance 115, producing a charge on the first electrode 902. The reference electrolyte 906 produces a charge at the second electrode 904. The wireless communication circuit 802 can measure a voltage difference between the first electrode 902 and the second electrode 904, determine the pH of the substance 115 based on the voltage difference, and report the pH to a wireless receiver via the antenna 510. The porous junction 910 can facilitate slow permeation of the reference electrolyte 906 into the substance 115, creating electrical contact between the reference electrolyte 906 and the substance 115. The reference electrolyte 906 can be periodically refilled via a fill hole 910 in the sensing device 120. The sensing device 120 can further include a magnet and/or ballast 810 allowing the sensing device 120 to function as an agitator and/or stabilizing the sensing device 120.

Figure 10:
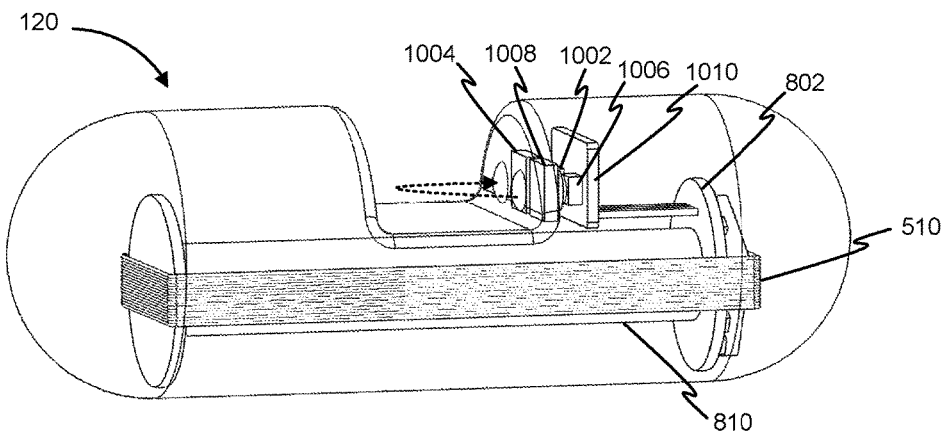
FIG. 10 illustrates an example sensing device configured as a wireless fluorescence sensor.

FIG. 10 illustrates an example sensing device 120 configured as a wireless fluorescence sensor. As shown in FIG. 10, the fluorescence sensor can include the wireless communication circuit 802, a LED light source 1006, an emission filter 1008, a light sensor 1002, a detection filter 1004, and an optics board 1010. A light signal passes from the LED light source 1006 through the emission filter 1008 into the substance 115. The substance 115 can fluoresce in proportion to concentrations of various compounds in the substance 115. The light signal emitted by the fluorescence passes through the detection filter 1004 and onto the light sensor 1002 to the optics board 1010, where the fluorescence can be measured. The optics board 1010 can communicate signals relating to fluorescence to the wireless communication circuit 802, which can transmit the data to a wireless receiver via the antenna 510. Based on the measured fluorescence, the wireless communication circuit 802 or an external device can determine the concentration of an analyte in the substance 115. The LED light source 1006 may be modulated in order to reduce interference from ambient light. The sensing device 120 can further include a magnet and/or ballast 810 allowing the sensing device 120 to function as an agitator and/or stabilizing the sensing device 120. A version of the sensing device 120 can function as a chemiluminescence sensor by using the light sensor 1002 and the detection filter 1004 to sense luminescence from the substance 115 and communicating the chemiluminescence value with the communication circuit 802 via the antenna 510.

Figure 11:
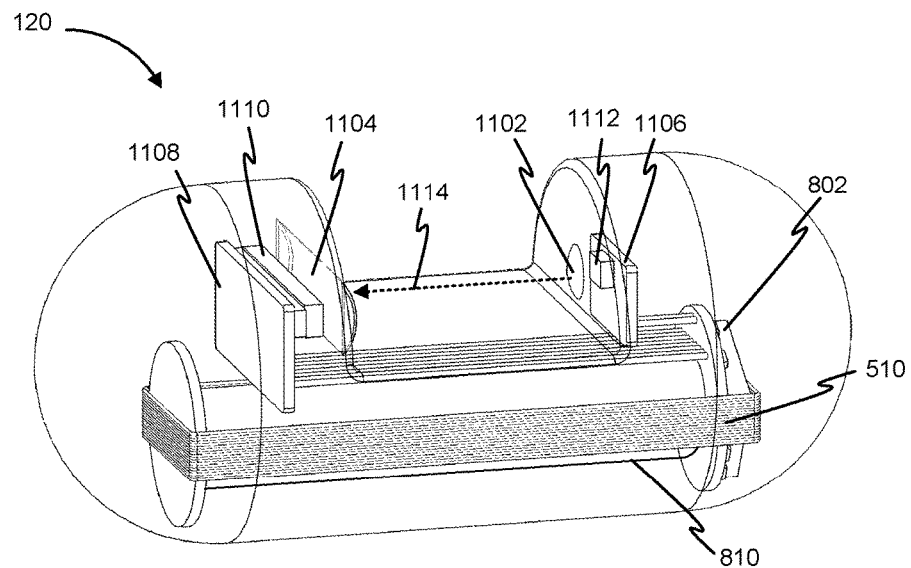
FIG. 11 illustrates an example sensing device configured as a wireless absorbance sensor.

FIG. 11 illustrates an example sensing device 120 configured as a wireless absorbance sensor. As shown in FIG. 11, the absorbance sensor can include the wireless communication circuit 802, a first lens 1102, a second lens 1104, a first optics board 1106, a second optics board 1108, and a linear variable filter 1110. The first optics board 1106 can include a white LED emitter 1112, which emits white light that passes through the first lens 1102 to the second lens 1104 along a light path 1114 through substance 115. The light can pass through the second lens 1104 to the linear variable filter 1110. After passing through the linear variable filter 1110, where the light is filtered, the second optics board 1108 can detect a magnitude of the signal and determine an amount of absorbance of the substance 115 based on the detected light by incorporating a photo diode array or a linear CMOS optical sensor. The second optics board 1108 can communicate signals relating to the absorbance to the wireless communication circuit 802, which can transmit the data to a wireless receiver via the antenna 510. Based on the measured absorbance, the wireless communication circuit 802 or an external device can determine the concentration of an analyte in the substance 115. The LED emitter 1112 may be modulated in order to reduce interference from ambient light. The sensing device 120 can further include a magnet and/or ballast 810 allowing the sensing device 120 to function as an agitator and/or stabilizing the sensing device 120.

Figure 12:
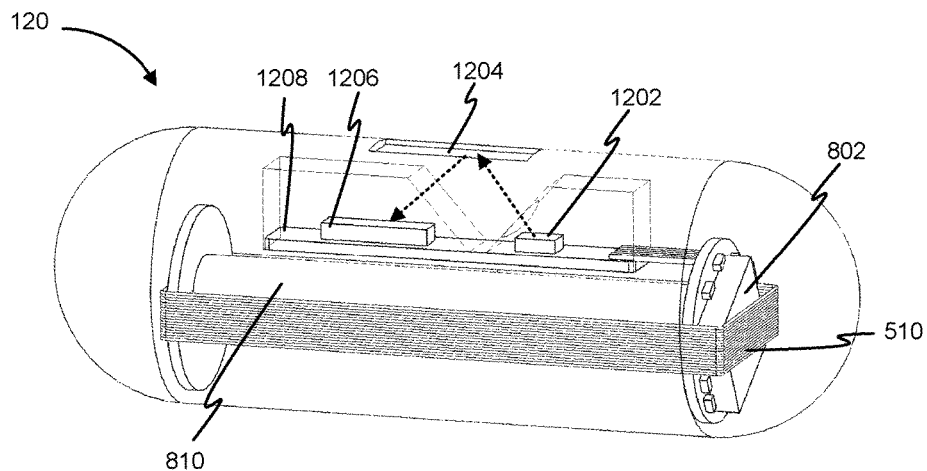
FIG. 12 illustrates an example sensing device configured as a wireless refractometer.

FIG. 12 illustrates an example sensing device 120 configured as a wireless refractometer. As shown in FIG. 12, the refractometer can include the wireless communication circuit 802, an LED light source 1202, a measurement window 1204, a linear array sensor 1206, and a circuit board 1208. The LED light source 1202 can emit a light signal toward the measurement window 1204, which can be a clear window allowing the light signal to reach the substance 115. The light signal can be refracted by the substance 115 and reflected towards the linear array sensor 1206. Based on where the reflected light hits the linear array sensor 1206, the circuit board 1208 can determine an index of refraction of the substance 115. The circuit board 1208 can send signals relating to the index of refraction to the wireless communication circuit 802, which transmits the index of refraction signals to a wireless receiver via the antenna 510. The LED light source 1202 may be modulated in order to reduce interference from ambient light. There may be an optical filter after the LED light source 1202 in order to reduce the wavelength projected onto the measurement window 1204 to a limited wavelength range. The sensing device 120 can further include a magnet and/or ballast 810 allowing the sensing device 120 to function as an agitator and/or stabilizing the sensing device 120.

Figure 13:
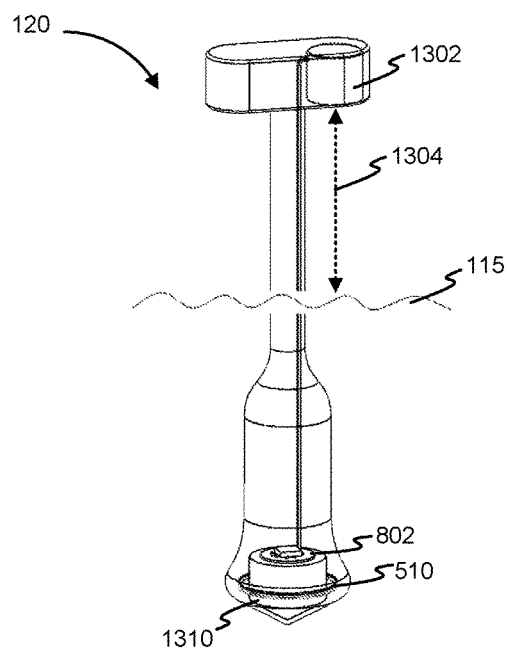
FIG. 13 illustrates an example sensing device configured as a wireless hydrometer.

FIG. 13 illustrates an example sensing device 120 configured as a wireless hydrometer. As shown in FIG. 13, the hydrometer can include the wireless communication circuit 802 and an ultrasonic sensor 1302. The sensing device 120 shown in FIG. 13 can float on the substance 115 at a height proportional to the specific gravity of the substance 115. The ultrasonic sensor 1302 can emit an ultrasound wave toward the surface of the substance 115 and detect a reflection of the emitted wave. The wireless communication circuit 802 can determine a distance 1304 between the ultrasonic sensor 1302 and the surface of the substance 115 based on the detected reflection, and calculate the specific gravity of the substance 115 based on the determined distance. The wireless communication circuit 802 can transmit the specific gravity to a wireless receiver via the antenna 510. The sensing device 120 can further include a ballast 1310 to stabilize the sensing device 120. The distance to the liquid can also be measured optically, alternatively, the level to which the sensing device is immerged into the liquid can be measured using resistive sensing pads or by optical means.

Regulating Properties based on Feedback

Figure 14:
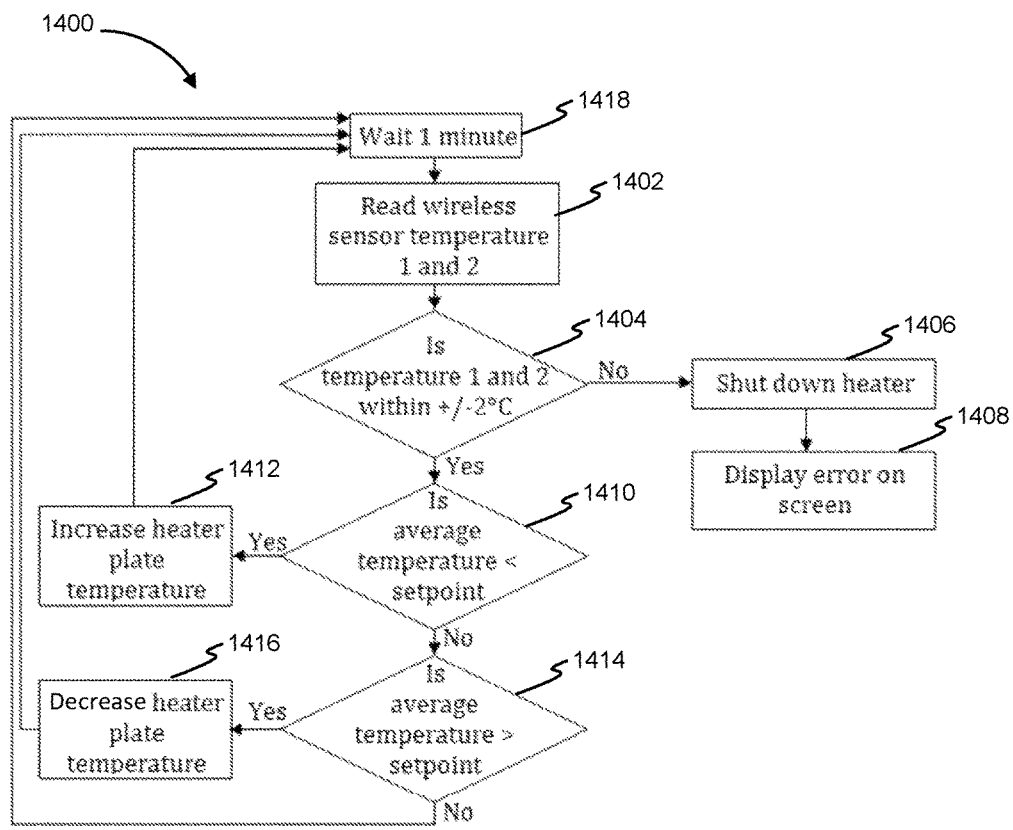
FIG. 14 is a flowchart illustrating an example process for regulating temperature of a substance based on feedback received from a wireless sensing device.

FIG. 14 is a flowchart illustrating an example process 1400 for regulating the temperature of the substance 115 based on feedback received from the wireless sensing device 120. The process 1400 is described with respect to the hot plate system 200, but a similar process can be used to regulate temperature in any other system. The process 1400 can be performed by the controller 226.

As shown in FIG. 14, the controller 226 can read 1402 the temperature from two sensors in the sensing device 120, such as the thermistor 504 and a temperature sensor in the integrated circuit 402. The controller 226 can determine 1404 whether a difference between the temperatures detected by the two sensors is within a threshold difference (e.g., +/−2° C.). If the difference is greater than the threshold difference, the controller 226 can shut down 1406 the heating element 216 and display 1408 an error on the control panel 224. If the difference is less than the threshold difference, the controller 226 can calculate an average of the two temperatures and determine 1410 whether the average is less than a setpoint. The controller 226 can compare a different temperature to the setpoint, such as the temperature output by one of the two sensors.

If the average temperature is less than the setpoint, the controller 226 can increase 1412 the heating element 216 temperature. If the controller 226 determines 1414 the average temperature is greater than the setpoint, the controller 226 can decrease 1416 the heating element 216 temperature. The controller 226 can compare the average temperature to two or more different setpoints. For example, the controller 226 can determine in step 1410 whether the average temperature is less than a lower setpoint, and determine in step 1414 whether the average temperature is greater than an upper setpoint. The controller 226 can then wait 1418 a specified amount of time, such as one minute, before repeating process 1400 to continue regulating the temperature of the substance 115. The wait time 1418 can be less than 1 minute.

Figure 15:
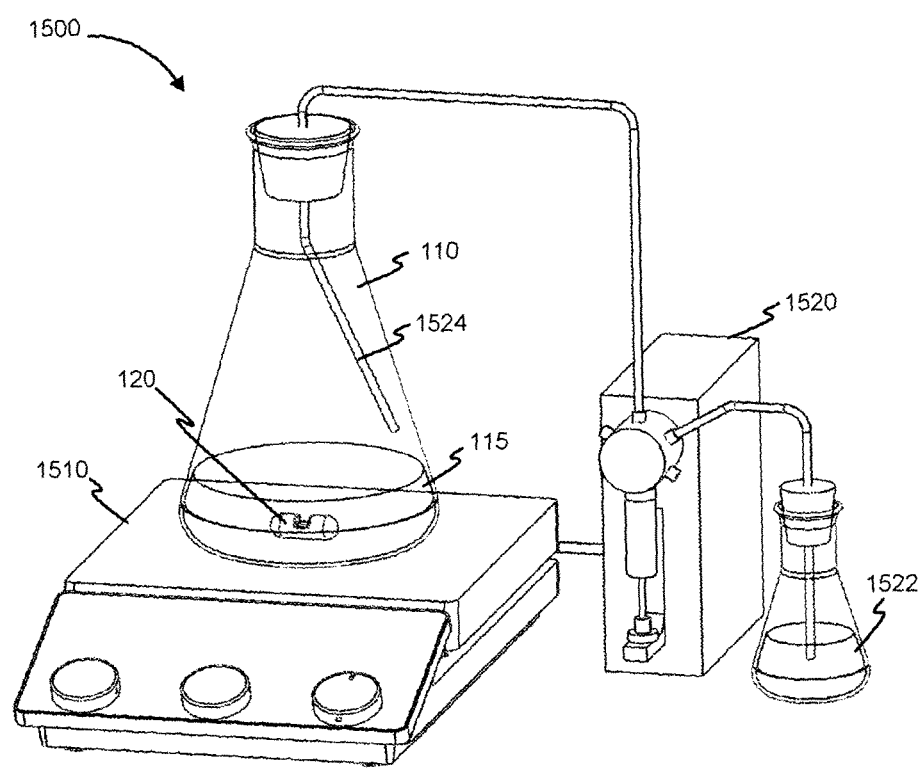
FIG. 15 illustrates an example system for controlling reagent delivery based on feedback received from a wireless sensing device.

FIG. 15 illustrates a system 1500 for controlling reagent delivery based on feedback received from the sensing device 120. As shown in FIG. 15, the system 1500 can include a control unit 1510 and a syringe dispenser pump 1520 configured to pump specified quantities of a reagent 1522 into the container 110 via the dispensing nozzle 1524. The sensing device 120 positioned in the substance 115 can measure one or more properties of the substance, such as fluorescence, absorbance, index of refraction, pH, an electrochemical signal, fluid level, or specific gravity, and wirelessly transmits data describing the measured properties to the control unit 1510. The control unit 1510 can be programmed with a desired setpoint for the measured property, and can be configured to control the syringe dispenser pump 1520 to deliver the reagent 1522 to the container 110 to achieve the desired setpoint.

For example, the setpoint can be a desired pH for the substance 115 and the reagent 1522 can be an acid or base. The control unit 1510 receives the pH measured by the sensing device 120 and compares the measured pH to the desired pH. If the measured pH is different from the desired pH, the control unit 1510 can cause the syringe dispenser pump 1520 to dispense a specified volume of the reagent 1522 into the container 110 until the desired pH is achieved. As another example, the setpoint can be a desired absorbance, fluorescence, or electrochemical signal, corresponding to a desired concentration of a particular compound in the substance 115 that can be altered by adding the reagent 1522. The control unit 1510 receives the absorbance, fluorescence, or electrochemical signal measured by the sensing device 120, and compares the received data to the setpoint. If the received data is different from the setpoint, the control unit 1510 can cause the syringe dispenser pump 1520 to dispense a specified volume of the reagent 1522 into the container 110 until the desired property is achieved.

The control unit 1510 and syringe dispenser pump 1520 can be incorporated into a single device instead of the two devices shown in FIG. 15. Furthermore, the control unit 1510 may control multiple syringe dispenser pumps 1520 to deliver multiple reagents 1522 to the substance 115. The system can also be configured to remove some or all of substance 115 from container 110, for example when a specific property of substance 115 has been achieved or to control the level of substance 115.

Methods for Use

Figure 16:
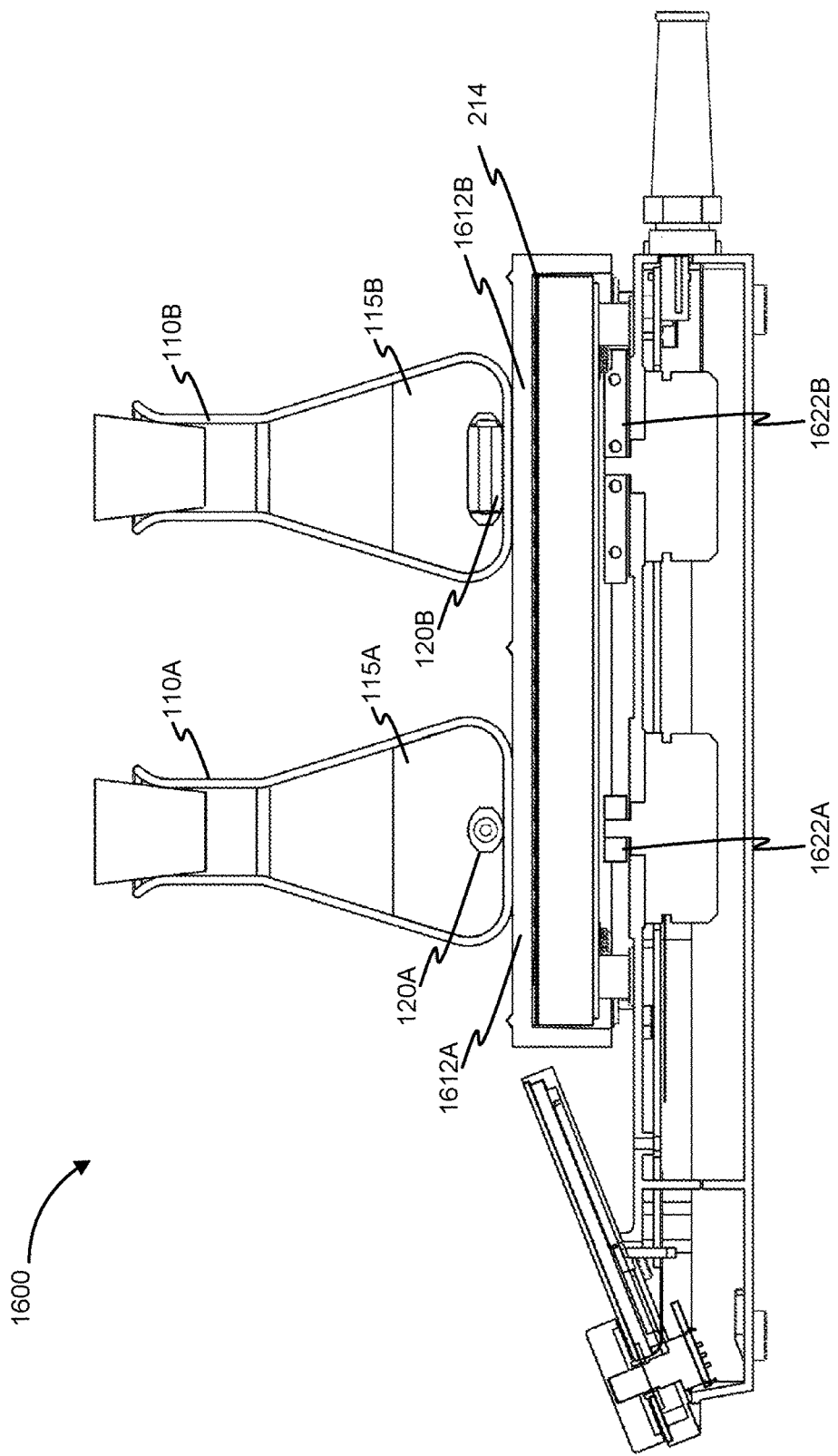
FIG. 16 illustrates an example hot plate system regulating properties of multiple substances.

FIG. 16 illustrates an example hot plate system 1600 including multiple containers 110A and 110B, as well as multiple sensing devices 120A and 120B. The first sensing device 120A can be rotated by a first magnet 1622A, agitating and measuring properties of a first substance 115A in the first container 110A as it is rotated. The second sensing device 120B can be rotated by a second magnet 1622B, agitating and measuring properties of a second substance 115B in the second container 110B as it is rotated. The first substance 115A can be heated by a first heating surface 1612A, and the second substance 115B can be heated by a second heating surface 1612B. The wireless receiver 214 receives data from the sensing devices 120A and 120B, from which outputs of the hot plate system 1600 can be controlled. For example, based on data received from the sensing device 120A, the hot plate system 1600 can increase or decrease the temperature of the first heating surface 1612A or can increase or decrease the rate of rotation of the first magnet 1622A.

Figure 17:
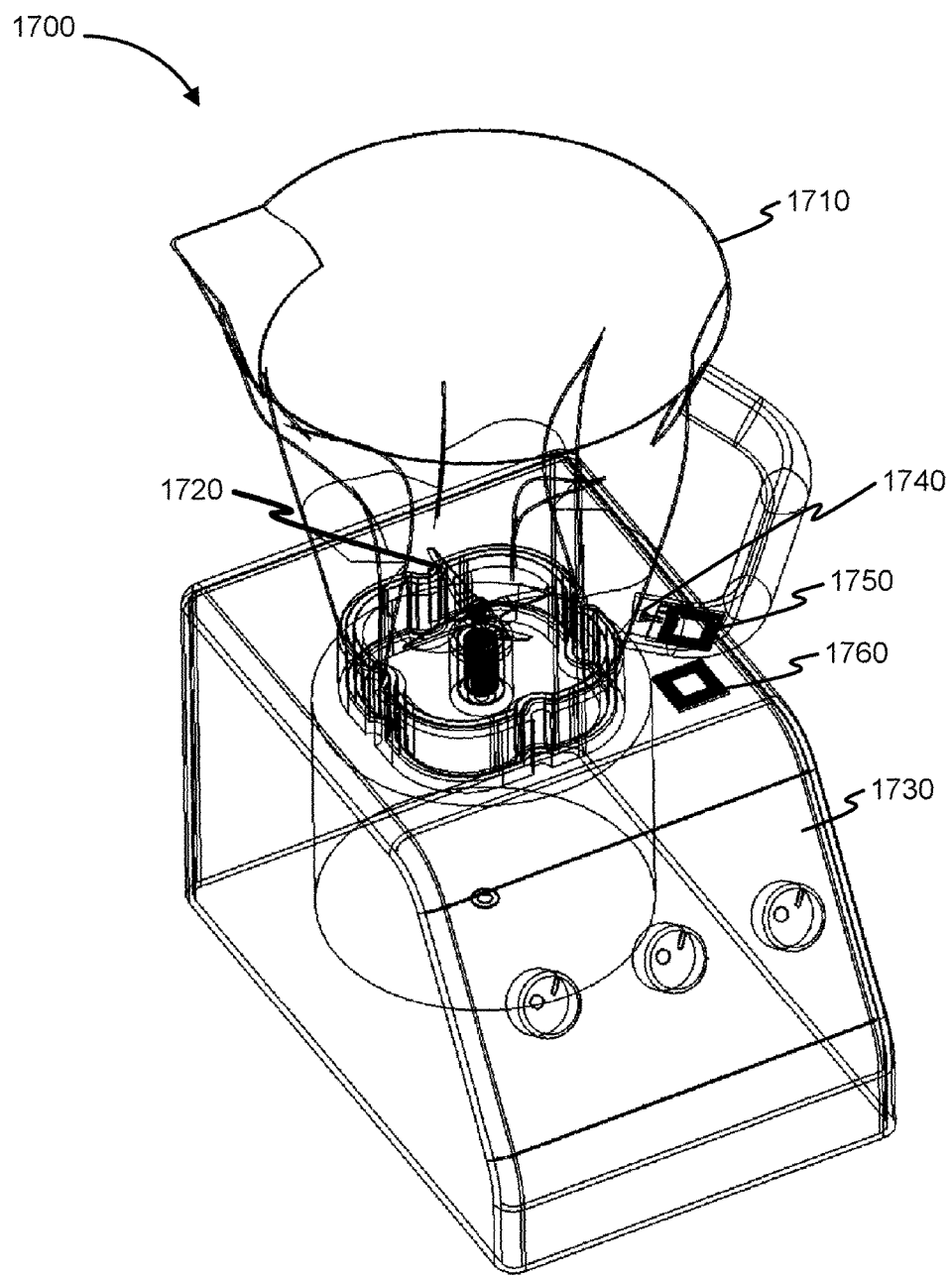
FIG. 17 illustrates an example blender system using a wireless sensing device.

FIG. 17 illustrates an example blender system 1700 including a wireless sensing device 120. In the example of FIG. 17, a blender pitcher 1710 can contain a substance to be blended (not shown). Blades 1720 can rotate within the blender pitcher 1710 to break up and blend the substance. The sensing device 120 can be incorporated into the blades 1720 to measure properties of the substance as it is blended. A control unit 1730 can receive user inputs to increase or decrease the rate of rotation of the blades 1720, and can receive feedback from the sensing device 120 to automatically increase or decrease the rate of rotation of the blades 1720 based on the detected properties of the substance in the blender pitcher 1710. Alternatively a temperature sensor 1740 built into the blender pitcher 1710 can detect temperature of the substance to be blended and via the antenna 1750 in the blender pitcher 1710 transmit the temperature information via a receiver antenna 1760 in the control unit 1730.

Figure 18A:
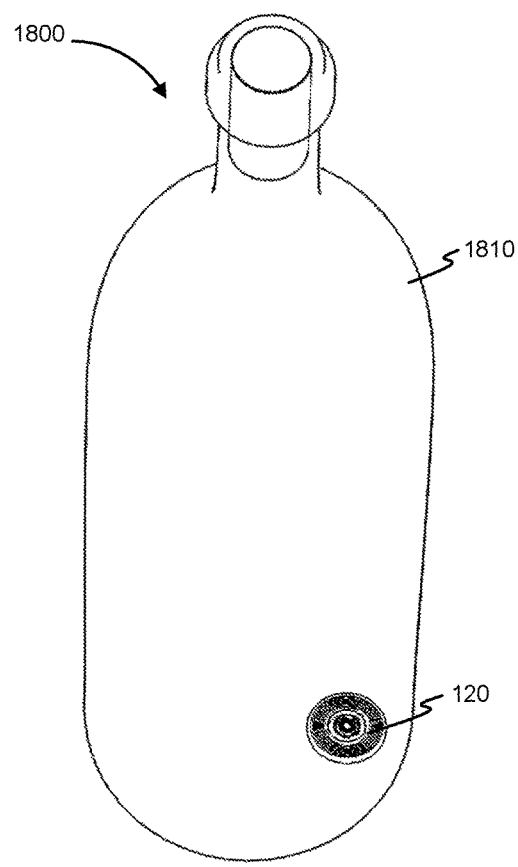
FIGS. 18A-18B illustrates an example wine monitoring system using a wireless sensing device.
Figure 18B:
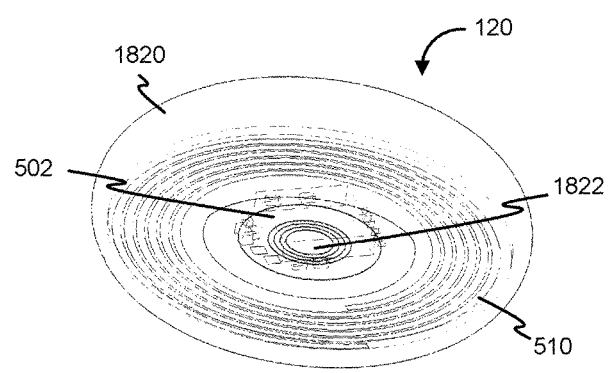

FIGS. 18A-18B illustrate an example wine monitoring system 1800. In the example of FIG. 18A, a wireless sensing device 120 can be placed in a wine bottle 1810 before the bottle is sealed and can monitor properties of the wine in the bottle 1810. The sensing device 120 can transmit the measured properties to an external wireless receiver, which can report the properties to a retailer or consumer. For example, the sensing device 120 may report a concentration of thiols, acetic acid, or oxygen in the wine. The retailer or consumer can use the reported information to determine the quality of the wine prior to opening the bottle 1810.

FIG. 18B illustrates an example of the sensing device 120 configured to detect sense properties of the wine that may indicate its quality. The configuration of the sensing device 120 shown in FIG. 18B can include a plastic overmold 1820 with an exposed electrochemical sensing area 1822 on its surface. The electrochemical sensing area 1822 can include one or more of the measuring electrode 804, the counter electrode 806, and the reference electrode 808 described with respect to FIG. 8, and can be configured to detect thiols, acetic acid, oxygen, or other relevant components of the wine. The sensing device 120 can also include the circuit board 502 for controlling operations and the antenna 510 for wireless communication with an external device.

Figure 19:
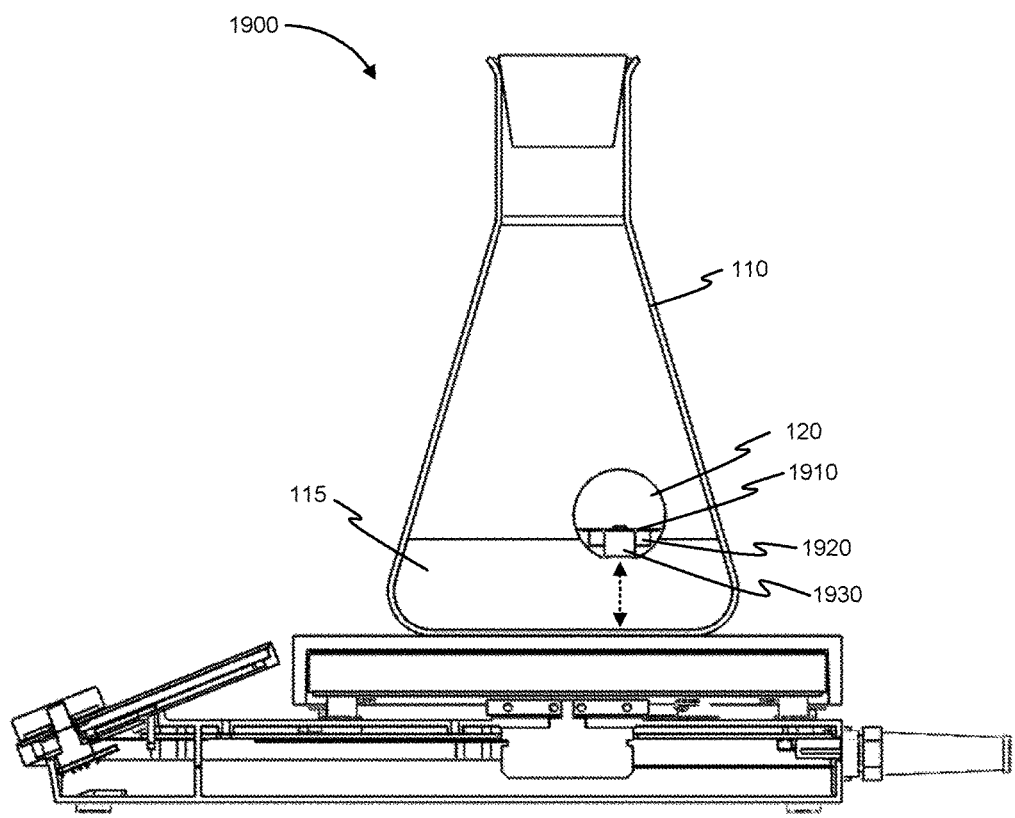
FIG. 19 illustrates an example floatable level sensing device.

FIG. 19 illustrates an example of the sensing device 120 configured to sense the fluid level of substance 115 in a container 110. The sensing device 120 uses an ultrasonic sensor 1930 coupled to a wireless communication circuit and antenna 1910. The sensing device 120 also contain a ballast 1920 for orienting the sensing device 120.

A wireless sensing device 120 as described herein can be used for numerous other applications. For example, a sensing device 120 can be used by a beer maker to remotely monitor the specific gravity of the beer. When the specific gravity reaches a specified quantity, an alert can be generated to notify the beer maker. As another example, a sensing device 120 can be used by an employee of a hospital or laboratory to verify whether sterilized or autoclaved substances reached a desired sterilization temperature. The sensing device 120 can monitor the temperature of the substances as they are autoclaved, and notify the employee whether the temperature inside the substance reached the sterilization temperature. In yet another example, a chef can monitor properties of food in a closed container using a sensing device 120 to determine precisely when the food reaches a desired temperature, viscosity, specific gravity, or combinations thereof. In another example a chemical reaction with multiple steps can be processed by using the sensing device 120 as a temperature sensor and as an agitator in the reaction compound where an instrument is programmed to expose the chemical compound to different temperature steps and agitation velocities for different periods of time and using the feedback from the sensing device 120 to set correct temperature in the various steps. In another example an industrial processing station can monitor the conductivity of a cleaning fluid and replace it if the conductivity gets above a specific value.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the disclosure.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the disclosure. Also, any optional feature of the variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application.

Nothing herein is to be construed as an admission that the present disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure.

We claim:

1. A method for heating and agitating a liquid in a container, comprising:
   positioning the container on a heating device, wherein the heating device comprises a heating element and a wireless receiver;
   positioning a submersible device in the liquid, wherein the submersible device comprises a first temperature measurement element and a wireless transmitter, and wherein the wireless transmitter is in communication with the wireless receiver, and wherein the communication between the wireless transmitter and the wireless receiver comprises communication by RFID, and wherein the wireless receiver is between the heating element and the submersible device;
   measuring a liquid temperature of the liquid with the first temperature measurement element;
   communicating the liquid temperature from the first temperature measurement element to a heating element controller;
   heating the liquid, wherein heating the liquid comprises activating the heating element by the heating element controller based on the liquid temperature communicated to the heating element controller; and
   agitating the liquid, wherein the submersible device comprises a first magnet, and wherein the heating device comprises a magnetic field creator, and wherein the magnetic field creator creates and alters a magnetic field exerting a magnetic force on the first magnet, and wherein the agitating the liquid comprises moving the submersible device in the liquid with the magnetic force on the first magnet.

2. The method of claim 1, wherein the magnetic field creator comprises a permanent magnet and a motor, wherein the motor is mechanically attached to the permanent magnet, further comprising rotating the permanent magnet with the motor.

3. The method of claim 1, wherein the magnetic field creator comprises one or more electromagnets.

4. The method of claim 1, further comprising setting a target temperature of the liquid with one or more controls on the heating device.

5. The method of claim 4, wherein when the liquid temperature communicated to the heating element controller is above the target temperature, a wireless computing device emits a notification.

6. The method of claim 1, further comprising setting a target temperature of the liquid, wherein when the liquid temperature communicated to the heating element controller is above the target temperature, the heating element controller de-activates the heating element.

7. The method of claim 1, further comprising setting a target temperature of the liquid, wherein when the liquid temperature communicated to the heating element controller is below the target temperature, the heating element controller activates the heating element.

8. The method of claim 1, wherein the heating element controller is in the heating device.

9. The method of claim 1, wherein the submersible device measures pH of the liquid.

10. The method of claim 1, wherein the submersible device measures specific gravity of the liquid.

11. The method of claim 1, wherein the submersible device measures viscosity of the liquid.

12. The method of claim 1, wherein the submersible device measures salinity of the liquid.

13. The method of claim 1, wherein the submersible device measures conductance of the liquid.

14. The method of claim 1, wherein the submersible device measures at least one property of the liquid, the at least one property of the liquid being any of color, fluorescence, or chemiluminescence.

15. The method of claim 1, wherein the submersible device measures absorbance of the liquid.

16. The method of claim 1, wherein the submersible device measures pressure of the liquid.

17. The method of claim 1, wherein the submersible device measures an electrochemical attribute of the liquid.

18. The method of claim 1, wherein the submersible device measures liquid level of the liquid.

19. The method of claim 1, wherein the submersible device measures rotation of the submersible device.

20. The method of claim 1, wherein the submersible device comprises a second temperature measurement element of a different type than the first temperature measurement element and where the temperature measurement of the first temperature measurement element and the second temperature measurement element is compared by the heating element controller and where the heating is terminated if a set difference is determined between the two temperature measurements thereby indicating a failure in the temperature measurement.

21. The method of claim 1, wherein the communication between the wireless transmitter and the wireless receiver comprises communication by a signal of 13.56 MHz.

22. The method of claim 1, wherein the submersible device comprises an analog to digital converter, and further comprising converting analog signals to digital signals, and transmitting the digital signals.

23. The method of claim 1, wherein the heating device comprises a WiFi module, and wherein the method further comprises communicating data from the WiFi module to a remote computing device.

24. The method of claim 1, wherein he submersible device is encased in EFEP.

25. The method of claim 1, further comprising delivering a reagent from a reagent delivery device, wherein the delivering comprises controlling the dispensing of the reagent based on data measured from and transmitted by the submersible device.

26. A method for heating and agitating a liquid in a container, comprising:
    positioning the container on a heating device having a heating surface, wherein the heating device comprises a heating element and a wireless receiver;
    positioning a submersible device in the liquid, wherein the submersible device comprises a first temperature measurement element and a wireless transmitter, and wherein the wireless transmitter is in communication with the wireless receiver, and wherein the communication between the wireless transmitter and the wireless receiver comprises communication by RFID, and wherein the wireless receiver is between the heating element and the heating surface;
    measuring a liquid temperature of the liquid with the first temperature measurement element;
    communicating the liquid temperature from the first temperature measurement element to a heating element controller;
    heating the liquid, wherein heating the liquid comprises activating the heating element by the heating element controller based on the liquid temperature communicated to the heating element controller; and
    agitating the liquid, wherein the submersible device comprises a first magnet, and wherein the heating device comprises a magnetic field creator, and wherein the magnetic field creator creates and alters a magnetic field exerting a magnetic force on the first magnet, and wherein the agitating the liquid comprises moving the submersible device in the liquid with the magnetic force on the first magnet.

27. The method of claim 26, wherein the communication between the wireless transmitter and the wireless receiver comprises communication by a signal of 13.56 MHz.

28. A method for heating and agitating a liquid in a container, comprising:
    positioning the container on a heating device having a heating surface, wherein the heating device comprises a heating element and a wireless receiver;
    positioning a submersible device in the liquid, wherein the submersible device comprises a first temperature measurement element and a wireless transmitter, and wherein the wireless transmitter is in communication with the wireless receiver, and wherein the communication between the wireless transmitter and the wireless receiver comprises communication by RFID, and wherein the wireless receiver is on top of the heating element;
    measuring a liquid temperature of the liquid with the first temperature measurement element;
    communicating the liquid temperature from the first temperature measurement element to a heating element controller;
    heating the liquid, wherein heating the liquid comprises activating the heating element by the heating element controller based on the liquid temperature communicated to the heating element controller; and
    agitating the liquid, wherein the submersible device comprises a first magnet, and wherein the heating device comprises a magnetic field creator, and wherein the magnetic field creator creates and alters a magnetic field exerting a magnetic force on the first magnet, and wherein the agitating the liquid comprises moving the submersible device in the liquid with the magnetic force on the first magnet.

29. The method of claim 28, wherein the communication between the wireless transmitter and the wireless receiver comprises communication by a signal of 13.56 MHz.

30. A method for heating and agitating a liquid in a container, comprising:
    positioning the container on a heating device having a heating surface, wherein the heating device comprises a heating element wireless receiver, wherein the heating element wireless receiver is a unitary element:
    positioning a submersible device in the liquid, wherein the submersible device comprises a first temperature measurement element and a wireless transmitter, and wherein the wireless transmitter is in communication with the heating element wireless receiver;
    measuring a liquid temperature of the liquid with the first temperature measurement element;
    communicating the liquid temperature from the first temperature measurement element to a heating element wireless receiver controller;
    heating the liquid, wherein heating the liquid comprises activating the heating element wireless receiver by the heating element wireless receiver controller based on the liquid temperature communicated to the heating element wireless receiver controller; and
    agitating the liquid, wherein the submersible device comprises a first magnet, and wherein the heating device comprises a magnetic field creator, and wherein the magnetic field creator creates and alters a magnetic field exerting a magnetic force on the first magnet, and wherein the agitating the liquid comprises moving the submersible device in the liquid with the magnetic force on the first magnet.

* * * * *